US006410545B2

(12) United States Patent
Uckun et al.

(10) Patent No.: US 6,410,545 B2
(45) Date of Patent: Jun. 25, 2002

(54) LIPID LOWERING QUINAZOLINE DIETARY SUPPLEMENT COMPOSITION

(75) Inventors: Fatih M. Uckun, White Bear Lake; Vuong N. Trieu, Roseville; Xing-Ping Liu, Minneapolis, all of MN (US)

(73) Assignee: Parker Hughes Institute, St. Paul, MN (US)

( * ) Notice: Subject to any disclaimer, the term of this patent is extended or adjusted under 35 U.S.C. 154(b) by 0 days.

(21) Appl. No.: 09/892,047

(22) Filed: Jun. 26, 2001

Related U.S. Application Data (63) Continuation of application No. 09/756,483, filed on Jan. 8, 2001, now Pat. No. 6,355,645, which is a continuation of application No. 09/126,940, filed on Jul. 30, 1998, now Pat. No. 6,172,071.

(51) Int. Cl.$^7$ .............................................. A61K 3/505
(52) U.S. Cl. ...................... 514/260; 514/259
(58) Field of Search .................. 514/260, 259

(56) References Cited

U.S. PATENT DOCUMENTS 6,172,071 B1    1/2001    Uckun et al.

FOREIGN PATENT DOCUMENTS

WO    WO 95/15758    6/1995

OTHER PUBLICATIONS

Higashino, T. et al., "Studies on the Reaction of Quinazoline with Aromatic Aldehydes in the Presence of Cyanide Ion", *Yakugaku Zasshi*, vol. 96, No. 4 (Abstract only) (1976).
Lempert–Sreter et al., Chemical Abstracts, vol. 93, entry 150203 (1980).
Lempert–Sreter et al., "Electron Deficient Heteroaromatic Ammonioamides. Part 26. N–(Quinazolin–3–io)amidates. Part 13. Phototransformations of an N–(Quinazolin–3–io)thioamidate and of a 10bH–1,3,4–thiadiazolo[3,2–c]quinazoline, the Ring Isomer of an N–(Quinazolin–3–io)thioamidate, and the Photochemical Formation of some 4,4'–Biquinazolinyls", *J. Chem. Soc. Perkin Trans.*, pp. 1143–1151 (1984).
Miyashita et al., Chemical Pham. Bull., vol. 40, No. 1, pp. 43–48 (1992).
Miyashita, A. et al., "Catalytic Action of Azolium Salts. IV. Preparations of 4–Aroylquinazolines and 4–Aroly–1H–pyrazolo[3,4–d]pyrimidines by Catalytic Action of 1,3–Dimethylimidazolium Iodide", *Chem. Pharm. Bull.*, vol. 42, No. 10, pp. 2017–2022 (Oct. 1994).
Miyashita et al., Heterocycles, vol. 40, No. 2, pp. 653–660 (1995).
Miyashita, A. et al., Chemical Abstracts, vol. 128, entry 270579 (1998).
Suzuki et al., Chemical Abstracts, vol. 128, entry 230337, (1998).
Suzuki, Y. et al., "Carbon–Carbon Bond Cleavage of α–Hydroxybenzylheteroarenes Catalyzed by Cyanide Ion: Retro–Benzoin Condensation Affords Ketones and Heteroarenes and Benzyl Migration Affords Benzylheteroarenes and Arenecarbaldehydes", *Chem. Pharm. Bull.*, vol. 46, No. 2, pp. 199–206 (Feb. 1998).
Taylor et al., Chemical Abstracts, vol. 80, entry 477718 (1974).

*Primary Examiner*—Theodore J. Criares
(74) *Attorney, Agent, or Firm*—Merchant & Gould P.C.

(57) ABSTRACT

A novel carbonyl-substituted quinazoline, preferably 4-(3'-bromobenzoyl)-6,7-dimethoxyquinazoline (WHI-P164), and methods for lowering blood cholesterol, including reducing total cholesterol and LDL-cholesterol levels by administration of the carbonyl quinazolines and compositions thereof.

3 Claims, 6 Drawing Sheets

FIG. 6A  A. Untreated
FIG. 6B  B. WHI-P164 x 1 mo
FIG. 6C  C. Vehicle x 1 mo
FIG. 6D

LIPID LOWERING QUINAZOLINE DIETARY SUPPLEMENT COMPOSITION

This application is a continuation of application Ser. No. 09/756,483, filed Jan. 8, 2001, now U.S. Pat. No. 6,355,645 which is a continuation of application Ser. No. 09/126,940, filed Jul. 30, 1998, now U.S. Pat. No. 6,172,071 B1, which patents are incorporated herein by reference.

FIELD OF THE INVENTION

This invention relates to novel quinazoline derivatives, for example 4-(3'-bromobenzoyl)-6,7-dimethoxyquinazoline), and methods of use. In particular, the compounds of the invention, when administered to a subject, are effective in reducing blood cholesterol levels in the subject.

BACKGROUND OF THE INVENTION

Atherosclerosis and ischemic heart disease remain the major cause of death of Americans. Elevated serum cholesterol levels present a major risk factor for atherosclerosis and related complications including myocardial infarction, heart failure, and cerebral stroke. Intervention studies performed in middle-aged men demonstrated a marked reduction in the incidence of cardiovascular events after the lowering of elevated total and low-density lipoprotein cholesterol (LDL-C) levels. The Cholesterol and Recurrent Events (CARE) trial and the Scandinavian Simvastatin Survival Study (4S)(1994, *Lancet* 344:1383–1389) have further shown that both women and elderly patients with prior history of ischemic heart disease benefit from cholesterol lowering therapy. (Miettinen et al., 1988, *Arch. Intern. Med.* 148:36–69; Sacks et al., 1996, *New Eng. J Med.* 335:1001–1009)

The most effective cholesterol lowering drugs are statins, which lower cholesterol levels by inhibiting 3-hydroxy-3-methylglutaryl coenzyme A (HMG-CoA) reductase, an enzyme which catalyzes the limiting step in cholesterol biosynthesis (Goldstein et.al., 1984, *J Lipid Res.* 25, 1450–1461). Compared to treatment regimens with other lipid lowering agents, such as the bile acid sequestrants (colestipol and cholestyramine), nicotinic acid, fibric acid (gemfibrozil and clofibrate), probucol, and experimental ACAT inhibitors, statin therapy has been found to bear several favorable features. Statins achieve extensive lowering of LDL-C, leading to an overall reduction in mortality, and are cost effective due to substantial reduction of hospital admissions and rates of coronary intervention. Statins also achieve better compliance than other treatments, as a result of their once-daily administration and few side effects. Combination of statins with other agents is considered necessary for patients with severe, complex or refractory lipid disorders. Furthermore, large clinical trials have suggested regression of atherosclerotic lesions by aggressive lipid lowering therapy (Schell and Myers, 1997, *Prog. on Cardiovascular Diseases* 39:483–496). To complement the statins and achieve successful reduction of cholesterol in statin-resistant subjects, identification of new lipid lowering agents with a different mechanism of action than statins remains a major focal point in contemporary atherosclerosis research. Since the HMG CoA inhibitors are ineffective in the mouse, this animal provides a useful model for screening novel agents capable of lowering cholesterol levels by a different mechanism of action than statins.

There is a need for new lipid lowering agents that are effective to lower total cholesterol and/or LDL-C, for the treatment of high cholesterol and other lipid disorders including those which are severe, complex, and/or refractory to current treatments.

SUMMARY OF THE INVENTION

Quinazoline compounds having a carbonyl substitution (carbonyl-Q) as described below and exemplified by 4-(3'-bromobenzoyl)-6,7-dimethoxyquinazoline (WHI-P164) have now been identified as a new class of potent cholesterol lowering agents. As shown in the Examples below, administration of the WHI-P164 reduces total cholesterol levels in hypercholesterolemic C57B⅙ mice on a high calorie diet by 23% and LDL-C by 45%. WHI-P164 also reduced total cholesterol levels and β-VLDL/LDL-cholesterol levels of hypercholesterolemic apolipoprotein E deficient mice (apo $e^{-/-}$) by 41% and 63%, respectively.

The present invention provides potent cholesterol-lowering agents, quinazoline compounds having a carbonyl group, (carbonyl-Q). An exemplary compound of the invention is 4-(3'-bromobenzoyl)-6,7-dimethoxyquinazoline).

The novel cholesterol lowering agents of the invention may be formulated by means known in the art for delivery to targeted areas of the body, including blood and/or gut, for example, by choice of carrier, mode of administration, or by conjugating carbonyl-Q with a specific targeting moiety, such as an antibody or ligand which binds a specific antigen or ligand receptor in the target tissue. Formulations useful for therapeutic reduction of cholesterol include injectable compositions, oral compositions, depot formulations, and the like containing an effective cholesterol-lowering amount of a carbonyl-Q compound of the invention, such as 4-(3'-bromobenzoyl)-6,7-dimethoxyquinazoline.

In the methods of the invention, carbonyl-Q cholesterol lowering agents such as 4-(3'-bromobenzoyl)-6,7-dimethoxyquinazoline are administered to a subject in order to modulate lipids in the blood, and particularly to lower blood cholesterol.

The above summary of the present invention is not intended to describe each disclosed embodiment or every implementation of the present invention. The examples and the detailed description which follow more particularly exemplify these embodiments.

DETAILED DESCRIPTION OF THE PREFERRED EMBODIMENTS

The invention includes a cholesterol lowering compound comprising a carbonyl substituted quinazoline (carbonyl-Q) exemplified by 4-(3'-bromobenzoyl)-6,7-dimethoxyquinazoline (WHI-P164) and a method for lowering blood cholesterol by administration of a carbonyl-Q.

Cholesterol-Lowering Compounds of the Invention

The cholesterol-lowering compounds of the invention include carbonyl-substituted quinazolines (carbonyl-Q) having the following general structural formula:

(carbonyl-Q)

where X is an alkyl (straight chain, branched, or cyclic) or is an aromatic ring structure, such as phenyl, napthyl, and the like. X may be substituted, for example, with a halogen, OH, SH, alkyl, alkoxy, acyloxy, NH$_2$, and the like. Carbonyl-Q may be substituted, for example, carbon or nitrogen atoms at positions 2, 5, 6, or 8 may have bound thereto halo, H, OH, alkyl, alkoxy, acyloxy, and the like groups.

An exemplary carbonyl-Q compound of the invention is 4-(3'-bromobenzoyl)-6,7-dimethoxyquinazoline (WHI-P164), having the following structure:

(WHI-P164)

The cholesterol-lowering compounds of the invention are formulated into compositions for administration, prefereably including a carrier which assists in the administration of the compound for cholesterol-lowering effects. For example, the composition may include a carrier which aids in suspending or solubilizing the compound of the invention or to improve the flavor or texture of the composition in foodstuffs or beverages for oral delivery to the gut. Alternatively, a composition containing the compound of the invention may include an isotonic carrier to facilitate delivery by injection, agents to prolong the half-life of the compound, and the like.

Multiple delivery systems are known for delivery of compounds to the bloodstream and gut of an animal. Preferably, the compound of the invention is administered to the gut, most preferably by oral delivery in a foodstuff composition, such as a dietary supplement or a staple foodstuff supplemented with the composition of the invention.

Mode of Administration

The cholesterol-lowering compounds of the invention can be formulated as pharmaceutical compositions, nutritional supplements, or as additives in foodstuffs and administered to a mammalian host, including a human in a variety of forms adapted for administration of a quinazoline compound. Preferred administration routes include intravenous, intramuscular, and subcutaneous injection. Most preferred is oral administration.

Solutions or suspensions of the cholesterol-lowering composition can be prepared in water, isotonic saline (PBS) and may preferably be mixed with a non-toxic surfactant. Dispersions may also be prepared in glycerol, vegetable oils, and the like. Under ordinary conditions of storage and use, these preparations may contain a preservative to prevent the growth of microorganisms.

The dose of the composition to be administered can vary widely in accordance with the age, size, and condition of the subject to be treated. Useful dosages of the composition are those which will deliver about 0.1 to about 500 mg/kg body weight/day, and preferably deliver about 0.5 to about 10 mg/kg body weight/day. The amount of the compound needed in the composition can vary with the mode of administration, e.g., by injection or by oral administration, to account for variance in the metabolism of the compound and of the composition.

While the invention is amenable to various modifications and alternative forms, specific embodiments of the invention are shown by way of the Examples and will be described in detail. It should be understood, however, that the intention is not to limit the invention to the particular embodiments described. On the contrary, the intention is to cover all modifications, equivalents, and alternatives falling within the spirit and scope of the invention.

EXAMPLES

The invention may be better understood by reference to the following Examples, that are not intended to limit the invention in any way.

Example 1

Animal Models of Hypercholesterolemia and Analytical Methods

Three- to four-week old C57B⅙ male mice (Taconic, Germantown, N.Y., USA) were kept in micro-isolator cages on a 12-hour day/night cycle and fed the Paigen's cocoa butter diet (15.8% fat, 1.25% cholesterol, and 0.5% sodium cholate) (Harlan Teklad, Madison, Wis., USA) for two weeks prior to initiation of lipid lowering therapy. Paigen's diet is described in Nishina et.al., 1993, *J. Lipid Res.* 34: 1413–1422.

Three- to four-week old apolipoprotein E deficient (apo $E^{-/-}$) mice were the progeny of breeding pairs of apo E knockout (apo EKO) mice obtained from Jackson Labs. (Bar Harbor, Me., USA). Mice were fed either regular rodent chow (5% fat and 0% cholesterol) (Teklad-LM 485, Harlan Teklad, Madison, Wis., USA), the Paigen's cocoa butter diet, or the Western diet (21.22% fat and 0.2% cholesterol) (Harlan Teklad, Madison, Wis., USA) for two weeks prior to treatment.

Animals were treated with test compounds by intraperitoneal injection daily for 7 days. A range of doses was administered. Control animals received vehicle alone. The effect of quinazoline derivatives on total cholesterol, LDL, HDL, liver enzymes, and glucose was analyzed. The mice tissues were also examined histologically.

Lipid determinations:

Serum total cholesterol was measured enzymatically using the cholesterol kit from Sigma Chemical Co. (St. Louis, Mo., USA). For liver tissue lipid measurements, lipids were extracted from homogenized hepatic tissues using the method of Bligh and Dyer (Bligh, et al., *Can. J. Biochem. Phys.* 1959, 37:911–917). One gram of liver tissue was homogenized in 1 ml of distilled water and extracted with 4 ml of chloroform/methanol (1:1, v/v). The chloroform phase containing the lipids was evaporated under a stream of nitrogen, the lipids dissolved in 100 $\mu$L of isopropanol, and subjected to cholesterol determination as described above. Triglyceride (TG) contents were determined using the TG kit from Sigma Chemical Co.

Serum cholesterol profiles were examined by Fast Protein Liquid Chromatography (FPLC) using 100 $\mu$l of serum per run. The serum was passed over two Superose™ 6 HR 10/30 connected in tandem equilibrated in phosphate buffered saline (PBS), using the FPLC system from Pharmacia Biotech (Piscataway, N.J., USA) consisting of a controller LCC-501 plus connected to a UV detector (UV-MII), two P500 pumps, and a Frac-100 fraction collector. The FPLC was remotely controlled and operated by the FPLC director program operated on an IBM computer. The system was operated at a flow rate of 0.5 ml/minute and fractions were collected at 0.5 ml/fraction. Cholesterol concentration of each fraction was determined as described above and plotted against the fraction numbers to obtain the serum cholesterol profile.

To determine the serum concentrations of LDL/$\beta$-VLDL and HDL, the sums of the LDL/$\beta$-VLDL peak (fractions 29–35) and the HDL peak (fractions 53–63) were divided by 0.1. To obtain the $IC_{50}$ and the minimum $\beta$-VLDL and HDL concentrations, the concentrations of $\beta$-VLDL and HDL were plotted against the dosage. Best fitted exponential decay curves were obtained using the equation: Concentration of HDL or LDL/$\beta$-VLDL=Aexp(−BX)+E, where A+E equals the concentration of HDL or LDL/$\beta$-VLDL at the dosage of 0 $\mu$g/day and E equals the mathematical minimum concentration of HDL or $\beta$-VLDL, and B equals $0.69/IC_{50}$. Best fitted curves were obtained using the Graphpad Inplot program, Graphpad Software, San Diego, Calif., USA.

Determination of In Vivo Hepatic VLDL-TG Production Using Triton WR1339

C57B⅙ and apoE-deficient mice were treated with intraperitoneal injections of 50 $\mu$l vehicle or 40 mg/kg WHI-P164 in 50 $\mu$l vehicle for 7 consecutive days, followed by a 36 hour fast to shut down intestinal chylomicron synthesis. Subsequently, mice were injected intravenously with 500 mg/kg Triton WR1339 (Sigma Chemical Co.) in 0.9% NaCl to completely inhibit their plasma VLDL clearance, as previously reported (Pasternali et al., 1996, *Ann. Intern. Med.* 125:529–540; Aalto-Setala et al., 1992, *J Clin. Invest.* 90:1889–1900). Blood samples were taken at 0 and 4 hours after Triton WR1339 injection and plasma TG levels were measured enzymatically using a commercially available enzymatic kit (Sigma Chemical Co.). Alternatively, food was returned to the mice after a 36 hour fast and blood samples were collected at 0, 1, 3, 6, and 9 hours after returning the food. Accumulation of chylomicron-TG was determined as accumulation of plasma TG.

Blood Chemistry

Serum levels alanine aminotransferase (ALT), alkaline phosphatase (ALP), lactate dehydrogenase (LDH), blood urea nitrogen (BUN), creatinine, creatinine phosphokinase (CPK), and glucose were determined by using a Synchron CX5 Clinical System (Beckman Instruments, Inc., Fullerton, Calif.) following manufacturer's instructions. For the glucose tolerance test, blood glucose levels were determined using the portable One Touch Profile glucose meter (Lifescan, Milpitas, Calif., USA).

Histopathology

At the end of the experiment, the animals were sacrificed and the harvested tissues were fixed in 10% phosphate buffered formalin overnight, embedded, sectioned, and stained by hematoxylin and eosin (H&E). The stained sections were examined for pathological changes. For Oil Red O staining, the liver was excised and snap frozen in liquid nitrogen. Five micrometer thick sections were obtained using the LeicaCM1800 cryostat (Heerbrugg, Switzerland), stained in 0.5% Oil Red O in propylene glycol for 1 hour, destained in 85% propylene glycol for 1 minute, rinsed twice in distilled water, counterstained in Mayer's hematoxylin for a few seconds, rinsed twice in distilled water, and mounted in Crystalmount (Biomedia Corp., Foster City, Calif.). The Oil Red O stainable material at 400 X magnification was quantitated using the ImagePro plus program (Media Cybernetics, Silver Spring, Md., USA) in conjunction with a 3CCD camera (DAGE-MTI Inc., Michigan City, USA).

Example 2

Chemical synthesis and Characterization of Quinazoline Derivatives

The common synthetic intermediate 4-chloro-6,7-dimethoxyquinazoline 5 used for synthesizing all the tested compounds by following literature procedures (Scheme 1). 4,5-dimethoxy-2-nitrobenzoic acid 1 was treated with thionyl chloride, and then reacted with ammonia to give 4,5-dimethoxy-2-nitrobenzamide 2 (Nomoto et al., 1990, *Chem. Pharm. Bull* 38: 1591–1595). The nitro group in compound 2 was reduced with sodium borohydride in the presence of copper sulfate (31) to give 4,5-dimethoxy-2-aminobenzamide 3, which was cyclized by refluxing with formic acid to give 6,7-dimethoxyquinazoline-4(3H)-one 4. The quinazolinone 4 was refluxed with phosphorus oxytrichloride to provide the key starting material 5 with good yield.

The lead compound 4-(3'-bromobenzoyl)-6,7-dimethoxyquinazoline WHI-P164 was synthesized by reacting 4-chloro-6,7-dimethoxyquinazoline 5 with the commercially available 3-bromobenzaldehyde in the presence of 1,3-dimethylimidazolium iodide and sodium hydride in refluxing dioxane for 4 hours (Scheme 2) (32,33). The remaining 6,7-dimethoxyquinazoline derivatives were synthesized by condensing 4-chloro-6,7-dimethoxyquinazoline 5 with the corresponding substituted anilines as shown in Scheme 3.

Scheme 1
Synthesis of the common synthetic intermediate,
4-chloro-6,7-dimethoxyquinazoline.

Scheme 2
Synthesis of WHI-P164.

Scheme 3
Synthesis of WHI-P97.

WHI-P97: 3'-Br, 4'-OH, 5'-Br
WHI-P111: 3'-Br, 4'-CH$_3$
WHI-P131: 4'-OH
WHI-P132: 2'-OH
WHI-P154: 3'-Br, 4'-OH
WHI-P197: 3'-Cl, 4'-OH

Synthetic Procedures and characterization data: All chemicals were purchased from Aldrich (Milwaukee, Wis.) or Sigma (St. Louis, Mo.) and were used without further purification. Except where distinguished, each reaction vessel was secured with a rubber septa, and the reaction was performed under nitrogen atmosphere. $^1$H and $^{13}$C NMR spectra were obtained on a Varian Mercury 300 instrument at ambient temperature in DMSO-d$_6$. Melting points were determined using a Fisher-Johns melting point apparatus and are uncorrected. FT-IR spectra were recorded on a Nicolet Protege 460 spectrometer. GC/MS was obtained on a HP 6890 GC System equipped with a HP 5973 Mass Selective Detector. TLC was performed on a precoated silica gel plate (Silica Gel KGF; Whitman Inc). Silica gel (200–400 mesh, Whitman Inc.) was used for all column chromatography separation.

4,5-Dimethoxy-2-nitrobenzamide 2. A suspension of 4,5-dimethoxy-2-nitrobenzoic acid 1 (2 g; 8.8 mmol) in SOCl$_2$ (10 mL) was stirred under reflux for 50 minutes. After cooling, the reaction mixture was poured into a mixture of concentrated NH$_4$OH (50 mL) and ice (30 g). The precipitate were collected by filtration, washed with water, and dried to give 1.85 g crude crystals. After recrystallization from DMF, 1.76 g pure product was obtained (88.5%). $^1$H NMR(DMSO-d$_6$): δ 7.60(s, 2H, —NH$_2$), 7.57(s, 1H , 6-H), 7.12(s, 1H , 3-H), 3.90, 3.87(s, s, 6H, —OCH$_3$); IR(KBr) υ$_{max}$: 3454, 2840, 1670, 1512, 1274, 1227 cm$^{-1}$; GC/MS m/z 226(M$^+$, 10.0), 178(98.5), 163(100.0), 135(51.0).

6,7-Dimethoxyquinazoline-4(3H)-one 4. NaBH$_4$ (400 mg) was added with stirring over 4 hours to a solution of 4,5-dimethoxy-2-nitrobenzamide 2 (1.58 g; 7 mmol) in MeOH containing catalytic amount of CuSO$_4$. The reaction mixture was poured into ice-water (200 mL) with stirring to give 4,5-dimethoxy-2-aminobenzamide 3 which was directly refluxed with HCOOH (20 mL) for 5 hours. After removal of solvent, the residue was recrystallized from DMF to give pure crystals 4 (1.18 g; 81.5 %). m.p. 295.0–297.0° C.; $^1$H NMR (DMSO-d$_6$): δ 12.03 (br, s, 1H, —NH) ,7.99 (s, 1H, 2-H), 7.42 (s, 1H, 5-H), 7.11 (s, 1H, 8-H), 3.88, 3.85 (s, s, 6H, —OCH$_3$); IR(KBr)υ$_{max}$: 3015, 2840, 1648, 1504, 1261, 1070 cm$^{-1}$; GC/MS m/z 206(M$^+$, 100), 191(M$^+$ —CH$_3$, 31.5), 163(16.7), 120(15.2).

4-Chloro-6,7-dimethoxyquinazoline 5. A suspension of 6,7-dimethoxyquinazoline-4(3H)-one 4 (12.36 g, 60 mmol) in POCl$_3$ (250 mL) was heated under reflux for 4 hr, when a clear solution was obtained. The POCl$_3$ was removed under reduced pressure, and the residue was dissolved in a mixture of CH$_2$Cl$_2$ and aqueous Na$_2$CO$_3$. The organic layer was dried and the solvent removed to give 4-chloro-6,7-dimethoxyquinazoline 5 (11.2 g, 83 %); m.p. 259.0–263.0° C.; $^1$H NMR (DMSO-d$_6$): d 8.75(s, 1H, 2-H), 7.53(s, 1H, 5-H), 7.25(s, 1H, 8H), 3.91( s, 3H, —OCH$_3$), 3.89( s, 3H, —OCH$_3$); IR (KBr) $\upsilon_{max}$: 2963, 2834, 1880, 1612, 1555, 1503, 1339, 1153, 962 cm$^{-1}$. GC/MS m/z 224(M$^+$, 100), 209(M$^+$ —CH$_3$, 9.4), 189(19.39), (69(10.55).

4-(3'-Bromobenzoyl)-6,7-dimethoxyquinazoline WHI-P164. Sodium hydride (108 mg; 4.5 mmol) was added to a stirred solution of 4 -chloro-6,7-dimethoxyquinazoline 5 (896 mg; 4 mmol), 3-bromobenzaldehyde (832 mg; 4.5 mmol) and 1,3-dimethylimidazolium iodide (336 mg; 1.5 mmol) in dioxane (30 mL) and the mixture was refluxed for 4 hours. The reaction mixture was cooled to room temperature, poured into ice-water, and precipitate was collected. The yield was 81.2% (1.05 g). m.p. 258.0–263.0 ° C.; $^1$H NMR (DMSO-d$_6$): d 9.25 (s, 1H, 2-H), 8.14 (s, 1H, 5-H), 7.92–7.43 (m, 4H , 2',4',5',6'-H), 7.40 (s, 1H, 8-H), 4.11 (s, 3H, —OCH$_3$), 4.00 (s, 3H, —OCH$_3$). IR (KBr) $\upsilon_{max}$: 3432, 1664, 1504, 1431, 1230 cm$^-$. GC/MS m/z 374(M$^+$ +1, 48.96), 373(M$^+$, 34.93), 372(M$^+$-1,47.67), 357 (58.74), 343(100.00), 293(M$^+$ -Br, 31.48), 189(26.27).

General procedures for compounds synthesized according to Scheme 3. A mixture of 4-chloro-6,7-dimethoxyquinazoline 5 (448 mg; 2 mmol) and the appropriately substituted aniline (2.5 mmol) in 20 ml of alcohol (EtOH or MeOH) was heated to reflux. Heating was continued for 4–24 hours, sufficient Et$_3$N was added to neutralize the solution, and the solvent was then concentrated to give crude product, which was recrystallized from DMF.

4-(3',5'-Dibromo-4'-hydroxylphenyl)-amino-6,7-dimethoxyquinazoline WHI-P97: yield: 72.80%; m.p. >300.0° C.; $^1$H NMR (DMSO-d6): δ 9.71 (s, 1H, —NH), 9.39 (s, 1H, —OH), 8.48 (s, 1H, 2-H), 8.07 (s, 2H, 2',6'-H), 7.76 (s, 1H, 5-H), 7.17 (s, 1H, 8-H), 3.94 (s, 3H, —OCH$_3$), 3.91 (s, 3H, —OCH$_3$); IR(KBr) $\upsilon_{max}$:3054 (br), 3419, 2868, 1627, 1512, 1425, 1250, 1155 cm-1; GC/MS m/z 456 (M$^+$+1.54.40), 455 (M$^+$, 100.00), 454 (M$^+$-1, 78.01), 439 (M$^+$ —OH, 7.96), 376 (M$^+$+1- Br, 9.76), 375 (M+-Br, 10.91), 360 (5.23).

4-(3'-Bromo-4'-methylphenyl)-amino-6,7-dimethoxyquinazoline WHI-P111. yield: 82.22 %; m.p.225.0–228° C. $^1$H NMR (DMSO-d$_6$): δ 10.23(s, 1H, —NH), 8.62(s, 1H, 2-H), 8.06(d, 1H, J$_{2',5'}$<2.1 Hz, 2'-H), 7.89(s, 1H, 5-H), 7.71(dd, 1H, J$_{5',6'}$=8.7 Hz, J$_{2',6'}$=2.1 Hz, 6'-H), 7.37(d, 1H, J$_{5',6'}$=8.7 Hz, 5'-H), 7.21(s, 1H, 8-H), 3.96(s, 3H, —OCH$_3$), 3.93(s, 3H, —OCH$_3$). IR(KBr) $\upsilon_{max}$: 3431, 3248, 2835, 1633, 1517, 1441, 1281, 1155 cm$^{-1}$. GC/MS m/z 375 (M$^+$+1,76.76), 374 (M$^+$-100.00), 373 (M$^+$-1,76.91), 358 (M$^+$+1—OH, 11.15), 357(1.42), 356 (6.31).

4-(4'-Hydroxylphenyl)-amino-6,7-dimethoxyquinazoline WHI-P131. yield: 84.29%; m.p. 245.0–248.0° C. $^1$H NMR (DMSO-d$_6$): d 11.21(s, 1H, —NH), 9.70(s, 1H, —OH), 8.74(s, 1H, 2-H), 8.22(s, 1H, 5-H), 7.40(d, 2H, J=8.9 Hz, 2',6'-H), 7.29(s, 1H, 8-H), 6.85(d, 2H, J=8.9 Hz, 3',5'-H), 3.98(s, 3H, —OCH$_3$), 3.97(s, 3H, —OCH$_3$). IR(KBr) $\upsilon_{max}$: 3428, 2836, 1635, 1516, 1443, 1234 cm$^{-1}$. GC/MS m/z 298 (M$^+$+1, 100.00), 297(M$^+$, 26.56), 296( M$^+$-1, 12.46).

4-(2'-Hydroxylphenyl)-amino-6,7-dimethoxyquinazoline WHI-P132. yield: 82.49%; m.p. 255.0–258.0° C.; $^1$H NMR (DMSO-d$_6$): d 9.78 (s, 1H, —NH), 9.29 (s, 1H, —OH), 8.33 (s, 1H, 2-H), 7.85 (s, 1H, 5-H), 7.41–6.83 (m, 4H, 3',4',5', 6'-H), 7.16 (s, 1H, 8-H), 3.93 (s, 3H, —OCH$_3$), 3.92 (s, 3H, —OCH$_3$); IR (KBr) $\upsilon_{max}$: 3500 (br), 3425, 2833, 1625, 1512, 1456, 1251, 1068 cm$^{-1}$; GC/MS m/z 298(M$^+$, +1,8.91), 297(M$^+$, 56.64), 281(M$^+$+1—OH, 23.47), 280 (M$^+$—OH, 100.00).

4-(3'-Bromo-4'-hydroxylphenyl)-amino-6,7-dimethoxyquinazoline WHI-P154. yield: 89.90%; m.p. 233.0–233.5° C.; $^1$H NMR(DMSO-d$_6$): δ 10.08(s, 1H, —NH), 9.38(s, 1H, —OH), 8.40(s, 1H, 2-H), 7.89(d, 1H, J$_{2',5'}$=2.7 Hz, 2'-H), 7.75(s, 1H, 5-H), 7.55(dd, 1H, J$_{5',6'}$=9.0 Hz, J$_{2',6'}$=2.7 Hz, 6'-H), 7.14(s, 1H, 8-H), 6.97(d, 1H, J$_{5',6'}$=9.0 Hz, 5'-H), 3.92(s, 3H, —OCH$_{ER}$), 3.90(s, 3H, —OCH$_3$); IR (KBr) $\upsilon_{max}$: 3431(br), 2841, 1624, 1498, 1423, 1244 cm$^{-1}$; GC/MS m/z 378(M$^+$+2, 90.68), 377(M$^+$+1, 37.49), 376(M$^+$, 100.00), 360(M$^+$3.63), 298(18.86), 282 (6.65).

4-(3'-Chloro-4'-hydroxylphenyl)-amino-6,7-dimethoxyquinazoline WHI-P197. yield 84.14%; m.p. 245.0° C.(dec); $^1$H NMR(DMSO-d$_6$): δ 10.00 (s, 1H, —NH), 9.37 (s, 1H, —OH), 8.41 (s, 1H, 2-H ), 7.78 (s, 1H, 5-H), 7.49 (d, 1H, J$_{2',5'}$=2.7 Hz, 2'-H), 7.55 (dd, 1H, J$_{5',6'}$=9.0 Hz, J$_{2',6'}$=2.7 Hz, 6'-H), 7.16 (s, 1H, 8-H), 6.97 (d, 1H, J$_{5',6'}$=9.0 Hz, 5'-H), 3.93 (s, 3H, —OCH$_3$), 3.91 (s, 3H, —OCH$_3$); IR (KBr) $\upsilon_{max}$: 3448, 2842, 1623, 1506, 1423, 1241 cm$^{-1}$; GC/MS m/z: 341(M$^+$, 100.00), 326(M$^+$-CH$_3$, 98.50), 310(M$^+$—OCH$_3$, 12.5), 295(9.0.), 189(13.5), 155 (13.8).

Example 3

Lipid Lowering Effects of WHI-P164 in Hypercholesterolemic C57B⅙ Mice.

A high cholesterol and high fat diet was used to induce hypercholesterolemia in C57B⅙mice, using the methods described by Paigen, et al. (Nishina, et al., 1993, *J. Lipid Res.* 34:1413–1422) and as described for Example 1. After two weeks, these mice exhibited a stable hypercholesterolemia with 4-times higher serum total cholesterol levels than control mice on regular rodent chow (451.4±14.8, n=69 versus 117.8±4.8, n=22, p<0.000 1). Hypercholesterolemic mice treated with WHI-P164 for one week at 1.6 mg/kg/day dose level exhibited a 23% reduction in mean serum total cholesterol levels (348.6±27.6 mg/dL, n=9 versus 451.4±14.8 mg/dL, n=69, p=0.02).

Figure 1:
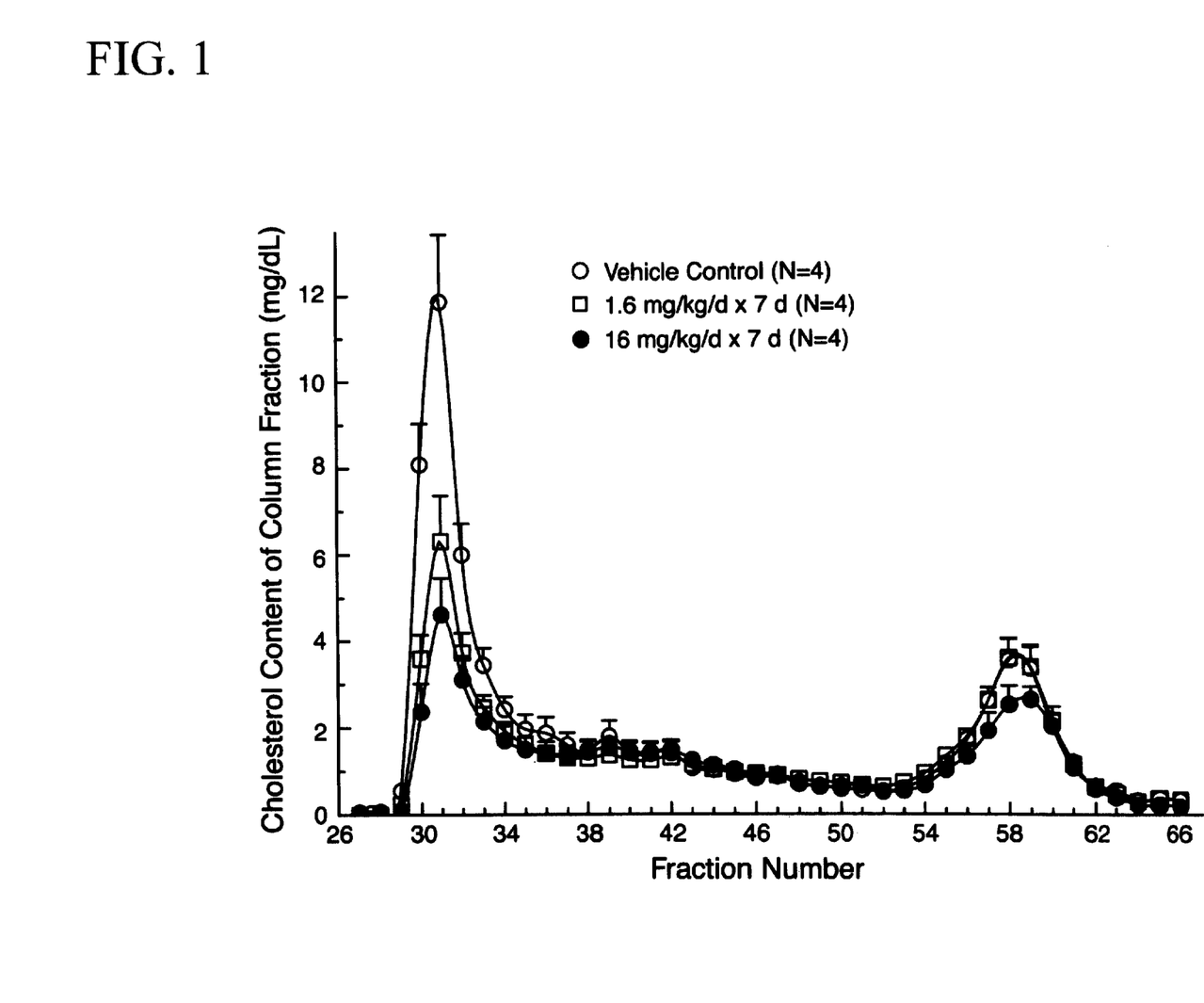
FIG. 1 is a graph showing the reduction of VLDL-C by WHI-P164 treatment in the C57B⅙ hypercholesterolemia model. Cholesterol profiles of C57B⅙ mice fed with a cocoa butter diet and 0 mg/kg/day (open circles); 1.6 mg/kg/day (open squares); or 16 mg/kg/day (closed circles) (n=4) are shown.

As shown by their serum lipoprotein profiles (FIG. 1), hypercholesterolemic C57B⅙ mice preferentially accumulated cholesterol rich VLDL (171±19 mg/dL, n=4 versus 7±4 mg/dL, n=3, p=0.0008) but no changes in HDL cholesterol levels (90±9 mg/dL, n=4 versus 86±13 mg/dL, n=3, p=0.8) (Table 2). WHI-P164 treatment caused a dramatic reduction of VLDL-C (FIG. 1). In WHI-P164 treated mice, serum VLDL-C decreased immediately from 171±19 mg/dL (n=4), to 99±13 mg/dL (n=4) at the 1.6 mg/kg/day dose level (P=0.02) and further decreased to 78±15 mg/dL (n=4) at the 16 mg/kg/day dose level (p=0.1) (Table 1). The calculated effective dose (ED$_{50}$) of WHI-P164 was 0.4 mg/kg/day with minimum serum VLDL-C level of 94±9 mg/dL. Thus, WHI-P164 was only able to reduce VLDL-C by 45%. WHI-P164 treatment did not significantly affect serum HDL-C levels (FIG. 1 and Table 1), even though there was a trend for decreasing HDL-C with increasing WHI-P164 dose levels.

TABLE 1

Reduction of VLDL-C by WHI-P164

|  | Dose (mg/kg) | N | VLDL-C (mg/dL) | p | HDL-C (mg/dL) | p |
|---|---|---|---|---|---|---|
| apo e[+/+] (C57B1/6) | | | | | | |
| Rodent Chow | 0.0 | 3 | 7 ± 4 | — | 86 ± 13 | — |
| Cocoa Butter | 0.0 | 4 | 171 ± 19 | — | 90 ± 9 | — |
| Diet | 1.6 | 4 | 99 ± 13 | 0.02 | 93 ± 8 | 0.8 |
|  | 4.0 | 4 | 106 ± 15 | 0.04 | 86 ± 5 | 0.7 |
|  | 8.0 | 3 | 101 ± 7 | 0.03 | 81 ± 9 | 0.5 |
|  | 16.0 | 4 | 78 ± 15 | 0.01 | 74 ± 10 | 0.3 |
| apo e[−/−] (C57B1/6) | | | | | | |
| Rodent Chow | 0.0 | 4 | 516 ± 158 | — | 21 ± 3 | — |
| Western diet | 8.0 | 8 | 190 ± 13 | 0.01 | 50 ± 10 | 0.09 |
|  | 0.0 | 3 | 1296 ± 118** | — | 50 ± 9 | — |
|  | 40.0 | 2 | 587 ± 4 | 0.02 | 90 ± 4 | 0.04 |

Plasma VLDL-C and HDL-C were calculated based on the lipoprotein profiles. Treated and untreated groups were compared by student t-test.
*P-values refer to differences between vehicle-treated and WHI-P164 treated mice.
**P = 0.01 for the difference of VLDL-C levels of apo e[−/−] via the rodent chos vs. western diet (1296 ± 118 mg/dL vs. 516 ± 58 mg/dL.

WHI-P164 treatment at the indicated dose levels, which were much lower than the highest nontoxic dose of 2 kg/kg, was not associated with any obvious clinical or laboratory signs of toxicity. In particular, liver enzymes (ALT, ALP, LDH) and BUN/Creatinine remained within normal limits (Table 2). Histopathologic examination of tissues did not reveal any drug related toxic lesions.

TABLE 2

Blood Chemistry of Treated C57B1/6 Mice

|  | 1 week | | 2 weeks | |
|---|---|---|---|---|
|  | +P164 | −P164 | +P164 | −P164 |
| Net weight change (g) | −0.26 ± 0.22 (n = 17) | 0.87 ± 0.33 (n = 10) | 1.88 ± 0.42 (n = 5) | 3.07 ± 0.50 (n = 10) |
| ALT (IU/L) | — | — | 148 ± 54 (n = 5) | 177 ± 19 (n = 10) |
| ALP (IU/L) | 101 ± 3 (n = 5) | 110 ± 9 (n = 5) | 94 ± 10 (n = 5) | 132 ± 6 (n = 10) |
| LD-L (IU/L) | 1402 ± 144 (n = 5) | 1533 ± 189 (n = 5) | 459 ± 83 (n = 5) | 426 ± 42 (n = 9) |
| BUN (mg/dL) | 25.4 ± 2.0 (n = 5) | 27.6 ± 2.0 (n = 5) | | |
| Glucose (mg/dL) | 201 ± 18 (n = 25) | 144 ± 9 (n = 24) | | |

Example 4

Lipid Lowering Effects of WHI-P164 in Hypercholesterolemic Apo E-Deficient Mice ApoE, a component of hepatic VLDL and intestinal chylomicron, controls the catabolism of these particles by serving as a ligand for LDL receptor and LDL-like receptor. Functionally defective apo e mutation is associated with type III dyslipoproteinemia, a condition mimicked by apo e[−/−] mice. As apo e[−/−] mice exhibited hypercholesterolemia even in the absence of dietary cholesterol supplementation due to a delayed clearance of hepatic VLDL particles, WHI-P164 was analyzed for its ability to reduce VLDL-C.

Figure 2:
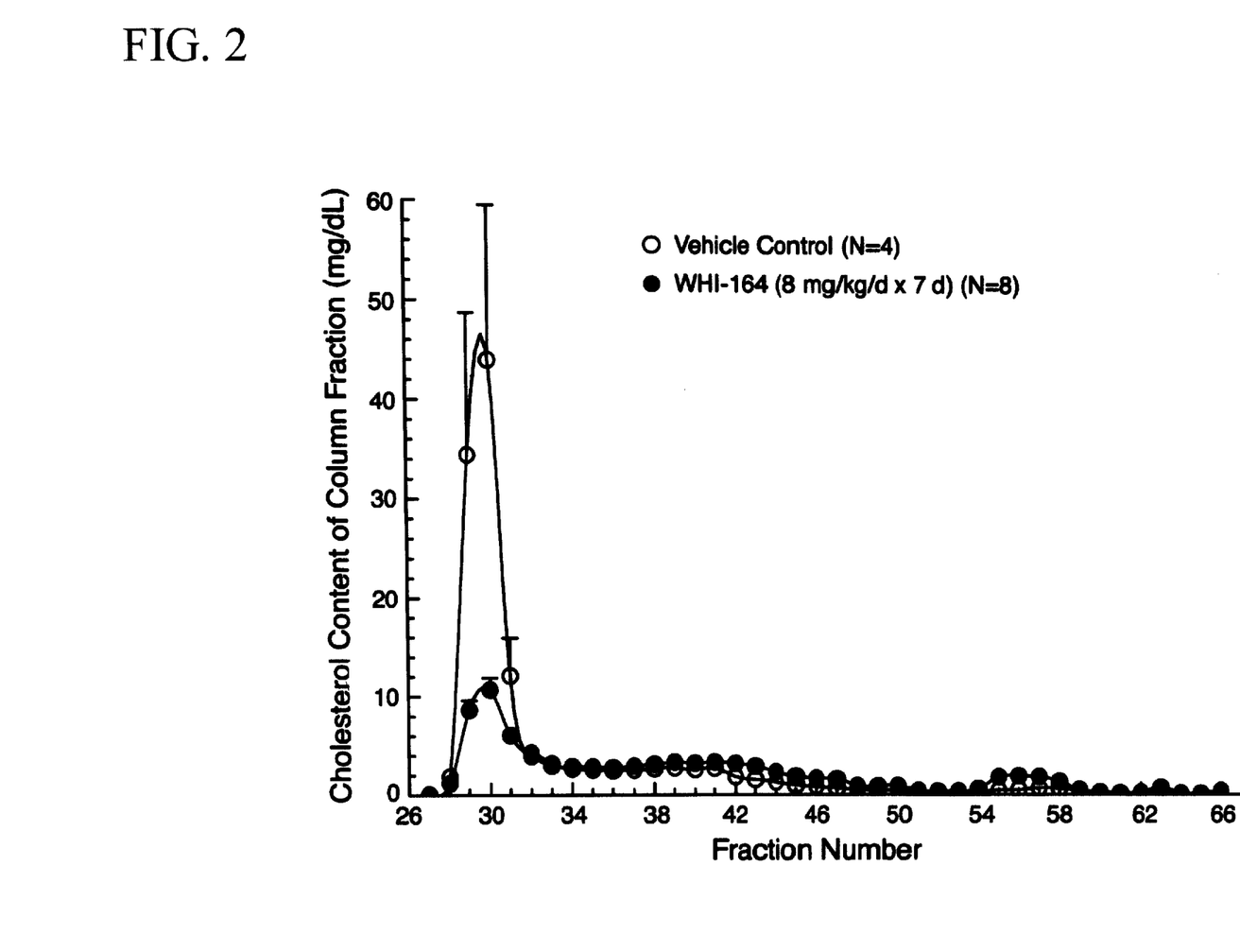
FIG. 2 is a graph showing reduction of VLDL-C by WHI-P 164 treatment in apo-$e^{-/-}$ mice fed on rodent chow and treated with WHI-P164 at 8 mg/kg/day for 7 days (closed circles, n=8) or with vehicle alone (open circles, n=4).

On regular rodent chow, the serum total cholesterol level of apo e[−/−] mice was 836±57 mg/dL (n=47). After one week therapy with 8 mg/kg/day WHI-P164 (n=12), the mean serum total cholesterol level was reduced to 551±29 mg/dL (p=0.02). Even in the absence of dietary cholesterol challenge, these apo e[−/−] mice exhibited higher VLDL-C (516±158 mg/dL, n=4 versus 7±4 mg/dL, n=3, p=0.04) and lower HDL-C levels than apo e[+/+] C57B⅙ mice on rodent chow (21±3 mg/dL, n=4 versus 86±13 mg/dL, n=3, p=0.0024) (Table 1). After one week therapy with 8 mg/kg/day WHI-P164, VLDL-C was decreased from 516±158 mg/dL, n=4, to 190±13 mg/dL, n=8, p=0.01 and HDL-C was slightly increased from 21±3 mg/dL, n=4, to 50±10 mg/dL (Table 1, FIG. 2).

Figure 3:
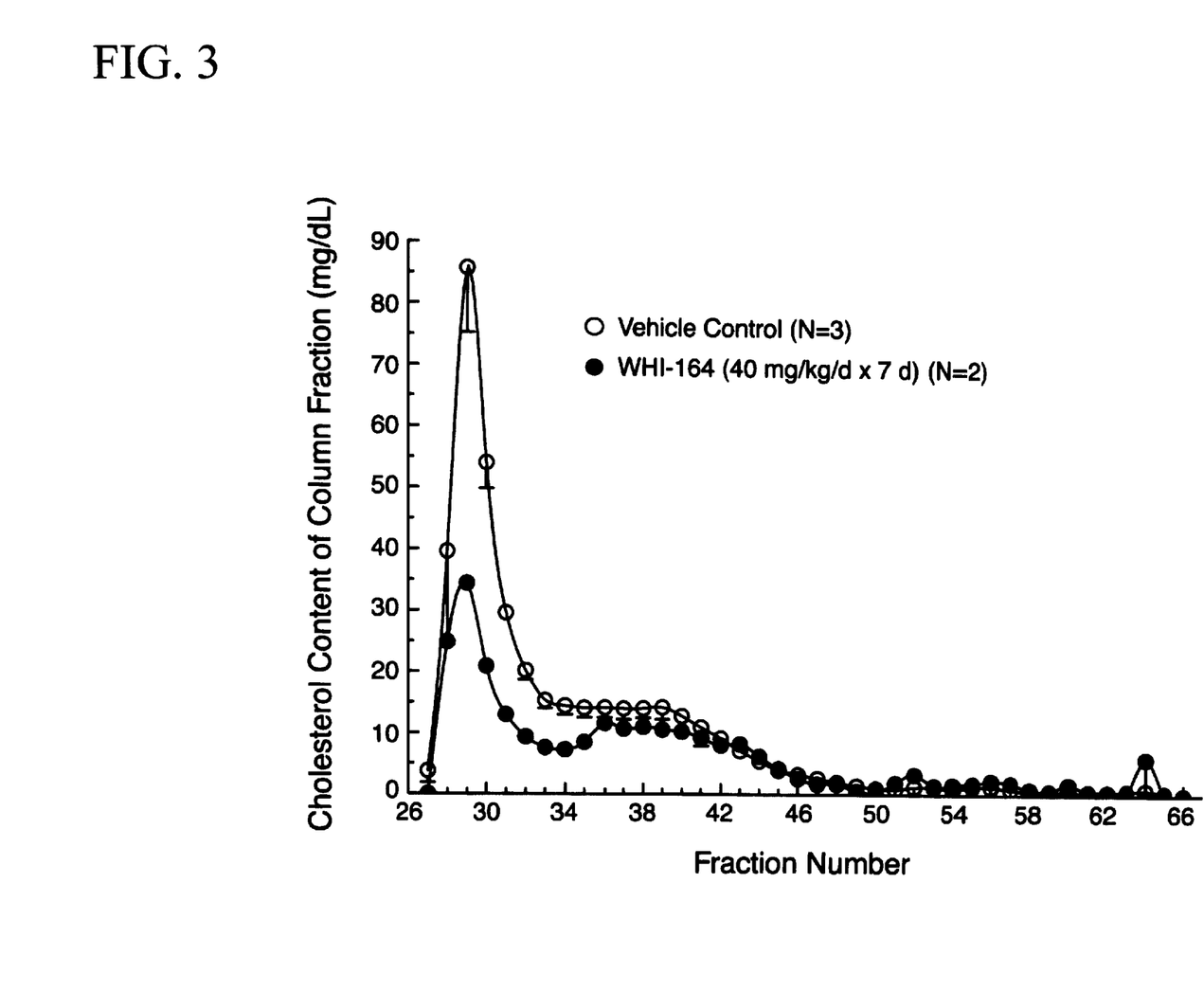
FIG. 3 is a graph showing reduction of VLDL-C by WHI-P164 treatment in apo-$e^{-/-}$ mice fed with a high fat, high cholesterol diet. Cholesterol profiles of apo-$e^{-/-}$ mice fed a Western diet and treated with WHI-P164 at 40 mg/kg/day for 7 days (closed circles, n=2) or with vehicle alone (open circles, n=3) are shown.
Figure 4A:
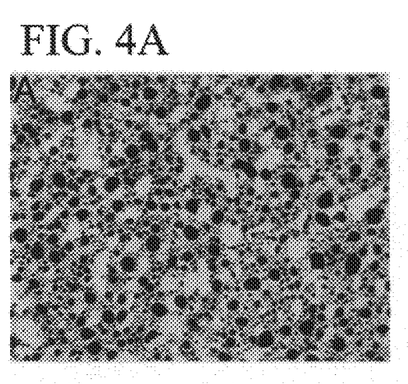
FIGS. 4A–4D are photographs showing reduction of hepatic triglyceride synthesis by WHI-P164 treatement. Livers of apo-$e^{-/-}$ mice fed a Western diet and treated with vehicle alone (FIGS. 4A and 4C) or with 1 mg/day of WHI-P164 for one week (FIGS. 4B and 4D) were analyzed using Oil Red O staining (FIGS. 4A and 4B) and Haemotoxylin and Eosin tissue section staining (FIGS. 4C and 4D).
Figure 4B:
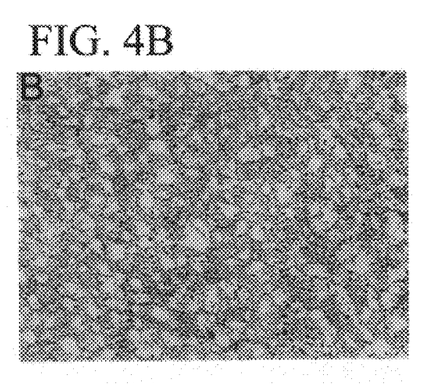
Figure 4C:
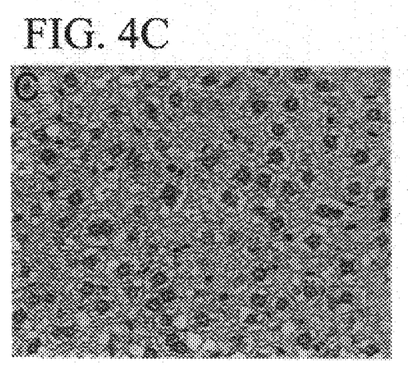
Figure 4D:
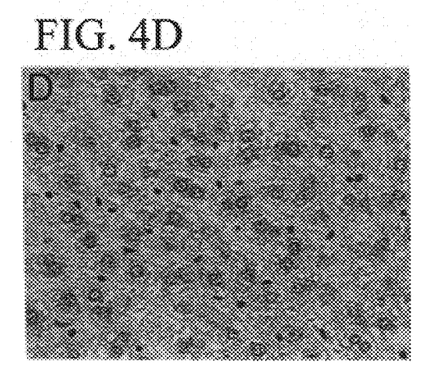

When challenged with a cholesterol-rich diet, these animals developed frank hypercholesterolemia due to delayed clearance of intestinal chylomicrons which shuttle the dietary cholesterol from the intestine to the liver. In the present study, all of the 46 ApoE-deficient mice that were fed Western diet (14) became severely hypercholesterolemic with a mean serum total cholesterol level of 1491±59 mg/dL. One week WHI-P164 therapy reduced the mean serum total cholesterol level of hypercholesterolemic apo e[−/−] mice to 1194±84 mg/dL (p=0.006) at a dose level of 8 mg/kg/day (n=19) and to 876±57 mg/dL (p<0.0001) at a dose level of 40 mg/kg/day (n=17) (Table 3). As shown in Table 1, dietary cholesterol challenge increased VLDL-C levels from 516±158 mg/dL, (n=3) to 1296±118 mg/dL (n=3), p=0.01. After one week of therapy with 40 mg/kg/day WHI-P164, VLDL-C was decreased from 1296±118 mg/dL, n=3, to 587±4 mg/dL, n=2, p=0.02 and HDL-C was slightly increased from 50±9 mg/dL, n=3, to 90±4 mg/dL, n=2, p=0.04 (Table 1, FIG. 3). In contrast to WHI-P164, other dimethoxyquinazoline derivatives did not exhibit cholesterol-lowering activity in C57B⅙ or apo e[−/−] mice (Table 4).

TABLE 3

Structure Function Evaluation of WHI-P164 and Other Dimethoxyquinazoline Derivatives

|  | [a]apo e[−/−] (C57B1/6) | | [b]apo e[+/+] (C57B1/6) | |
|---|---|---|---|---|
| Compounds | N | Cholesterol (mg/dL) | N | Cholesterol (mg/dL) |
| Vehicle | 46 | 1491 ± 59 | 69 | 451 ± 15 |
| WHI-P97 | 5 | 1129 ± 46 | 10 | 413 ± 18 |
| WHI-P111 | 5 | 1425 ± 92 | 4 | 406 ± 11 |
| WHI-P131 | 4 | 1532 ± 77 | 5 | 433 ± 20 |
| WHI-P132 | 5 | 1774 ± 61 | — | ND |
| WHI-P154 | 5 | 1492 ± 110 | — | ND |
| WHI-P164 | 17 | 876 ± 57* | 9 | 349 ± 28** |
| WHI-P197 | 5 | 1621 ± 146 | 5 | 372 ± 20 |

[a]apo e[−/−] (C57B1/6) mice were placed on Western diet for two weeks, followed by treatment with the drug for 1 week at 40 mg/kg/day.
[b]apo e[+/+] (C57B1/6) mice were placed on Cocoa butter diet for two weeks, followed by treatment with the drug for 1 week at 1.6 mg/kg/day.
*p < 0.0001
**p = 0.02.

WHI-P164 therapy, at either 8 mg/kg/day or 40 mg/kg/day, was not associated with any obvious clinical or laboratory signs of toxicity. In particular, liver enzymes (ALT, AST, ALP, LDH), CPK levels, and BUN/Creatinine remained within normal limits. Histopathologic examination of tissues did not reveal any drug related toxic lesions.

Example 5

Effects of WHI-P164 on Triglyceride (TG) Synthesis apo e[−/−] mice accumulate large amounts of TG-rich lipid droplets in their livers, due a blocked VLDL-TG secretion (Kuipers et al., 1997, *J. Clin. Invest.* 100:2915–2922). Treatment with 40 mg/kg/day WHI-P164 for 1 week signicantly reduced the Oil Red O stainable lipid material in the livers of Apo E-deficient mice that were fed on a Western diet (FIGS. 4A—4D). Image analysis demonstrated a 75% reduction of lipid material in treated mice (658±256 red pixels/field, n=1 1 versus 2590±401 red pixels/field, n=12; p=0.0007). When tissue lipids were measured, there was a 22% reduction in hepatic cholesterol 39% reduction in hepatic triglycerides. As shown in Table 4, the reduction in hepatic TG accumulation was not due to depletion of precursors for hepatic TG accumulation, namely plasma free fatty acid (FFA) and triglyceride.

TABLE 4

Analysis of Tissue Lipids

| Lipid Levels | WHI-P164 | Control (vehicle) | p Value |
|---|---|---|---|
| hepatic cholesterol (mg/g wet wt) | 51.4 ± 4.4 (n = 7) | 65.9 ± 5 (n = 8) | p = 0.5 |
| hepatic triglycerides (mg/g wet wt) | 211.6 ± 27 (n = 7) | 349.3 ± 34 (n = 8) | p = 0.008 |
| plasma FFA (mM) | 3.6 ± 0.3 (n = 12) | 3.2 ± 0.3 (n = 11) | |
| plasma TG (mg/dL) | 165 ± 19 (n = 15) | 167 ± 14 (n = 17) | |

Example 6

Regression of Pre-existing Atherosclerotic Lesions

Figure 6A:
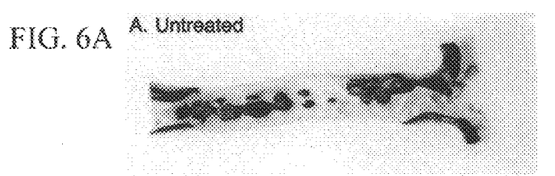
FIGS. 6A-D demonstrate WHI-P164 induced regression of pre-existing atherosclerotic lesions in hypercholesterolemic apo-e$^{-/-}$ mice. Aortas from untreated (FIG. 6A), vehicle treated (FIG. 6B), and WHI-P164 treated (FIG. 6C) animals were stained with Sudan IV to show the fatty streaks. Aortas of untreated control mice were obtained at 7 months to reflect the pretreatment condition of the test groups. Aortas of vehichle treated or WHI-P164 treated test mice were obtained at 8 months following a one month treatment program. Statistical comparisons indicate **p= 0.002 for untreated controls versus WHI-P164 treated test mice and p=0.007 for vehicle controls versus WHI-P164 treated mice.
Figure 6B:
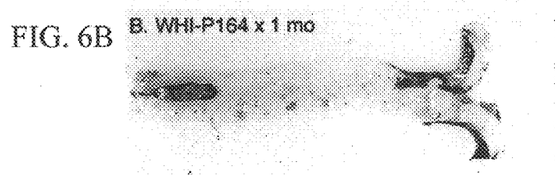
Figure 6C:
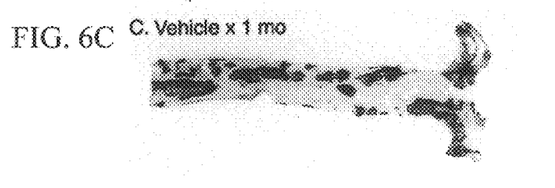
Figure 6D:
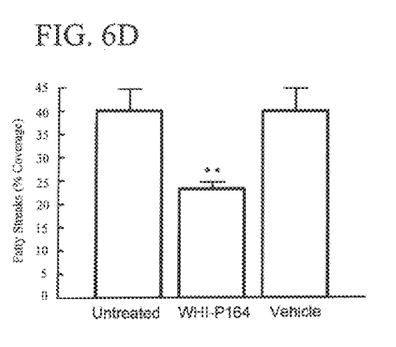

The effectiveness of WHI-P164 against pre-existing atherosclerotic lesions in apo $e^{-/-}$ mice kept 7 months on high fat Western diet was examined. apo $e^{-/-}$ mice were treated with either vehicle control or WHI-P164 at 40mg/kg/day for one month. As shown in FIG. 6A, before treatment, fatty streaks stainable by Sudan IV covered 40±5% (n=3) of the aortic surface of these mice. Treatment with WHI-P164 caused a marked regression of the atherosclerotic lesions with fatty streaks covering only 23±2% (n=7) of the aortic surface (FIG. 6B), as compared to 40±5% in untreated mice (n=3) (FIG. 6A) (p=0.002) and 40±5% in the vehicle-treated mice (n=8) (FIG. 6C) (p=0.007).

Example 7

Effect of WHI-P164 on Liver Lipoprotein Synthesis Determination of In Vivo Hepatic VLDL-TG Production Using Triton WR1339

To determine if WHI-P164 prevent hepatic TG accumulation by relieving 9 block in VLDL-TG secretion or by inhibiting upstream TG synthesis, in vivo hepatic VLDL-TG synthesis was analyzed. Synthesis was determined by following the accumulation of VLDL-TG after shutting down VLDL catabolism with Triton WR1339 injection and intestinal chylomicron synthesis with a 36 hours fast.

C57B⅙ and apoE-deficient mice were treated with intra peritoneal injections of vehicle or 40 mg/kg WHI-P164 (in 50 μl vehicle) for 7 consecutive days, followed by a 36 hour fast to shut down intestinal chylomicron synthesis. Subsequently, mice were injected intraperitonealy (i.p.) with 500 mg/kg Triton WR1339 (Sigma Chemical Co.) in 0.9% NaCl to completely inhibit their plasma VLDL clearance, as previously reported (Kuipers et al., 1996, *Heptology* 24:241–247). Blood samples (50 μl) were taken at 0 and 4 hours after Triton WR1339 injection and plasma TG was measured enzymatically using a commercially available enzymatic kit (Sigma Chemical Co.), as previously reported (Kuipers, supra).

WHI-P164 treated apo $e^{-/-}$ mice exhibited significantly less accumulation of VLDL-TG than vehicle-treated control mice after Triton WR1339 treatment (p=0.0002), although they exhibited similar pre-Triton WR1339 serum triglyceride levels (Table 5). WHI-P164 treated C57B⅙ mice also exhibited significantly less accumulation of VLDL-TG than vehicle-treated control mice (p=0.003), although they exhibited similar pre-Triton WR1339 serum triglyceride levels (Table 5). The data support the hypothesis that WHI-P164 inhibited TG synthesis, thereby preventing hepatic accumulation of TG in apo $e^{-/-}$ mice.

TABLE 5

Inhibition of Hepatic VLDL-TG Synthesis by WHI-P164

| | Triglyceride (mg/dL) | |
|---|---|---|
| | Pre-Triton WR 1339 | Post-Triton WR 1339 |
| apo $e^{-/-}$ (C57B1/6) | | |
| Vehicle | 110 ± 12 (n = 8) | 744 ± 37 (n = 14) |
| WHI-P164 | 155 ± 14 (n = 10) | 465 ± 46 (n = 8)* |
| apo $e^{+/+}$ (C57B1/6) | | |
| Vehicle | 143 ± 6 (n = 5) | 1354 ± 44 (n = 12) |
| WHI-P164 | 124 ± 12 (n = 5) | 1031 ± 95 (n = 8)** |

Hepatic VLDL-TG was determined as accumulation of triglyceride after injection of Triton WR1339, which shuts down VLDL catabolism, and 36 hours fast which shuts down intestinal chylomicron synthesis. Student t-test was used to compare the WHI-164 treated group versus the vehicle treated group.
*p = 0.0002
**p = 0.003

Figure 5:
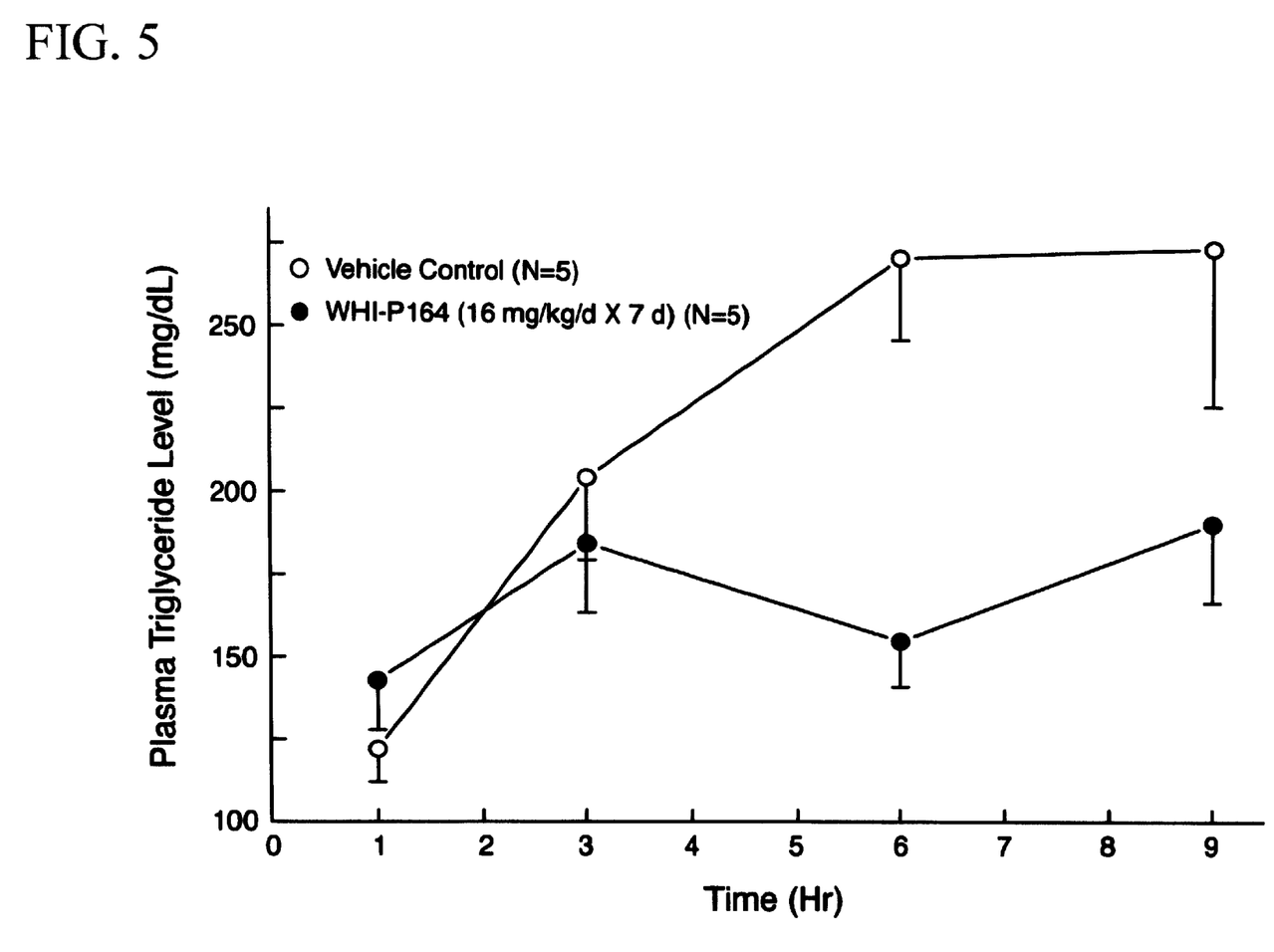
FIG. 5 is a graph showing inhibition of postprandial triglyceride accumulation by WHI-P164 treatment. C57B⅙ mice were treated with WHI-P164 at 40 mg/kg/day for 7 days, and fasted 36 hours with continuing treatment. Food was readministered at 0, 1, 3, 6, and 9 hours. WHI-P164 treated mice (closed circles) exhibited much reduced postprandial triglyceride accumulation in comparison to vehicle treated mice (open circles).

The decrease in TG synthesis was not specific to the liver, as intestinal chylomicron-TG was also inhibited by WHI-P164 therapy. When 36 hours fasted mice were fed again, they immediately consumed the food and exhibited a time dependent accumulation in plasma TG, due to intestinal chylomicron-TG synthesis. Postprandial accumulation was inhibited by WHI-P164 therapy (FIG. 5). Inhibition reached statistical significance at 6 hours in vehicle treated mice having a plasma TG level of 272±25 mg/dL, n=5, as compared to a plasma TG level of 155±32 mg/dL, n=5, p=0.004 in WHI-P164 treated mice.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

All publications and patent applications in this specification are indicative of the level of ordinary skill in the art to which this invention pertains. All publications and patent applications are herein incorporated by reference to the same extent as if each individual publication or patent application was specifically and individually indicated by reference.

We claim:

1. A dietary supplement composition comprising: a compound of the formula:

wherein X comprises a straight or branched chain or cyclic alkyl, or an aromatic ring structure, and wherein each of $R_1$–$R_5$ are independently selected from H, OH, $NH_2$, SH, alkyl, alkoxy, and acyloxy; and and acceptable nutrients.

2. The dietary supplement composition according to claim 1, wherein the compound has the formula:

wherein each of $R_1$–$R_3$ independently comprise H, OH, alkoxy, acyloxy, SH, $NH_2$ or halo.

3. The dietary supplement composition according to claim 1, wherein the compound is 4-(3'-bromobenzoyl)-6,7-dimethoxy quinazoline.

* * * * *

UNITED STATES PATENT AND TRADEMARK OFFICE
CERTIFICATE OF CORRECTION

PATENT NO. : 6,410,545 B2
DATED : June 25, 2002
INVENTOR(S) : Uckun et al.

It is certified that error appears in the above-identified patent and that said Letters Patent is hereby corrected as shown below:

<u>Title page,</u>
Item [63], Related U.S. Application Data, after "...now U.S. Pat. No. 6,172,071.", insert the following sentence:

-- Applicants have filed herein a Terminal Disclaimer under 37 C.F.R. .sctn. 1.321(c) to disclaim the terminal part of any patent granted on this application Serial No. 09/892,047 which would extend beyond the expiration date of U.S. Pat. No. 6,172,071. --

<u>Column 3,</u>
Line 22, "vehichle" should read -- vehicle --

Signed and Sealed this

Twenty-fourth Day of December, 2002

JAMES E. ROGAN
*Director of the United States Patent and Trademark Office*